(12) United States Patent
Pellemans et al.

(10) Patent No.: US 7,403,293 B2
(45) Date of Patent: Jul. 22, 2008

(54) METROLOGY APPARATUS, LITHOGRAPHIC APPARATUS, PROCESS APPARATUS METROLOGY METHOD AND DEVICE MANUFACTURING METHOD

(75) Inventors: Henricus Petrus Maria Pellemans, Veldhoven (NL); Arie Jeffrey Den Boef, Waalre (NL); Wilhelmus Maria Corbeij, Eindhoven (NL); Hans Van Der Laan, Veldhoven (NL)

(73) Assignee: ASML Netherlands, Veldhoven (NL)

( * ) Notice: Subject to any disclaimer, the term of this patent is extended or adjusted under 35 U.S.C. 154(b) by 35 days.

(21) Appl. No.: 11/478,300

(22) Filed: Jun. 30, 2006

(65) Prior Publication Data

US 2007/0013921 A1 Jan. 18, 2007

Related U.S. Application Data

(63) Continuation-in-part of application No. 11/170,746, filed on Jun. 30, 2005.

(51) Int. Cl.
*G01B 9/02* (2006.01)
*G01B 11/02* (2006.01)
(52) U.S. Cl. ..................... 356/521; 356/497
(58) Field of Classification Search ............. 356/479, 356/497, 521, 511–515
See application file for complete search history.

(56) References Cited

U.S. PATENT DOCUMENTS 5,703,692 A 12/1997 McNeil et al.
5,880,838 A 3/1999 Marx et al.
5,963,329 A 10/1999 Conrad et al.
6,608,690 B2 8/2003 Niu et al.
6,699,624 B2 3/2004 Niu et al.
6,704,661 B1 3/2004 Opsal et al.
6,721,691 B2 4/2004 Bao et al.
6,738,138 B2 5/2004 Wei
6,753,961 B1 6/2004 Norton et al.
6,768,983 B1 7/2004 Jakatdar et al.
6,772,084 B2 8/2004 Bischoff et al.
6,785,638 B2 8/2004 Niu et al.
6,813,034 B2 11/2004 Rosencwaig et al.
6,819,426 B2 11/2004 Sezginer et al.
6,856,408 B2 2/2005 Raymond
6,919,964 B2 7/2005 Chu (Continued)

FOREIGN PATENT DOCUMENTS

EP 1 455 235 A2 9/2004

(Continued)

OTHER PUBLICATIONS

Teipel et al., "Characteristics of Supercontinuum Generation in Tapered Fibers Using Femtosecond Laser Pulses," Appl. Phy. B 77, pp. 245-251 (2003).

(Continued)

*Primary Examiner*—Patrick J Connolly
(74) *Attorney, Agent, or Firm*—Pillsbury Winthrop Shaw Pittman, LLP (57) ABSTRACT

A metrology apparatus for measuring a parameter of a microscopic structure on a substrate, the apparatus comprising a supercontinuum light source arranged to generate a measurement beam, an optical system arranged to direct the measurement beam onto the substrate and a sensor for detecting radiation reflected and/or diffracted by the structure.

32 Claims, 4 Drawing Sheets

U.S. PATENT DOCUMENTS

| | | |
|---|---|---|
| 6,928,628 B2 | 8/2005 | Seligson et al. |
| 6,972,852 B2 | 12/2005 | Opsal et al. |
| 6,974,962 B2 | 12/2005 | Brill et al. |
| 6,987,572 B2 | 1/2006 | Lakkapragada et al. |
| 7,046,376 B2 | 5/2006 | Sezginer |
| 7,061,615 B1 | 6/2006 | Lowe-Webb |
| 7,061,623 B2 | 6/2006 | Davidson |
| 7,061,627 B2 | 6/2006 | Opsal et al. |
| 7,068,363 B2 | 6/2006 | Bevis et al. |
| 2002/0030826 A1 | 3/2002 | Chalmers et al. |
| 2003/0214730 A1 | 11/2003 | Wang et al. |
| 2004/0119970 A1 | 6/2004 | Dusa et al. |
| 2005/0099627 A1 | 5/2005 | Zhao et al. |
| 2006/0033921 A1 | 2/2006 | Den Boef et al. |
| 2006/0066855 A1 | 3/2006 | Den Boef et al. |
| 2006/0126074 A1 | 6/2006 | Van Der Werf et al. |
| 2006/0139592 A1 | 6/2006 | Den Boef et al. |
| 2006/0158659 A1 * | 7/2006 | De Lega et al. ............. 356/497 |

FOREIGN PATENT DOCUMENTS

EP            1455235 A2 *   9/2004

OTHER PUBLICATIONS

Fink et al., "Advanced Technologies for Optical Frequency Control and Optical Clocks," Muri-Technology for Optical Frequency Control and Optical Clocks, (2003), 35 pgs.

Giessen, Ultrafast Nano-Optics, Generation of Whitelight Supercontinua in Tapered Optical Fibers, Apr. 17, 2005, 3 pages including Abstract.

www.imra.com, Femtolite Series Annexed as mht 3.1 and mht 3.2, Femtolite Series—"A" Model, Femtolite Series—"B" Model, Femtolite Series—"C" Model, Femtolite Series-Tunable, Femtolite Series-Supercontinuum, 19 pages.

Bouwhuis, G., et al., Principles of Optical Disc Systems, (1985), The Complex Amplitude Grating, Sections 2.2.3, pp. 16-23; Numerical Results, Section 2.3.4, pp. 38-49.

European Search Report issued in EP Appl. No. 06 25 3180 dated Oct. 16, 2006.

* cited by examiner

METROLOGY APPARATUS, LITHOGRAPHIC APPARATUS, PROCESS APPARATUS METROLOGY METHOD AND DEVICE MANUFACTURING METHOD

RELATED APPLICATIONS

This application is a continuation-in-part of U.S. application Ser. No. 11/170,746 filed Jun. 30, 2005, the entire contents of which is hereby incorporated by reference.

FIELD

The present invention relates to a metrology device, in particular one that can be used in a lithographic apparatus, in a process apparatus or as a stand-alone device and a metrology method, in particular that can be used as part of a device manufacturing method.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

During and after various steps in the production of devices using lithographic methods, it is necessary to make measurements on the devices that have been produced to assess whether the production process has proceeded correctly. Such measurements are collectively referred to as metrology. In view of the scale of devices produced by lithography, metrology methods generally involve illuminating the device structure or a test structure with a measurement beam and detecting the returning radiation. One such method is scatterometry, in particular angle-resolved scatterometry in which the spectrum of the radiation reflected by the structure under inspection is measured at different angles using a sensor such as a CCD in the pupil plane of an objective lens.

The sensitivity and speed of operation of most metrology devices is limited by the radiation source used to generate the measurement beam. Presently available sources include: Xe lamps, which have a good, wide bandwidth but poor luminance and poor spatial coherence; SLED lasers, which have good luminance and spatial coherence but not a particularly wide bandwidth and are not capable of generating wavelengths below about 400 nm.

SUMMARY

It is desirable to provide a metrology apparatus with improved sensitivity and/or speed of operation.

According to an aspect of the invention, there is provided a metrology apparatus for measuring a parameter of a microscopic structure on a substrate, the apparatus comprising a supercontinuum light source arranged to generate a measurement beam, an optical system arranged to direct the measurement beam onto the substrate and a sensor for detecting radiation reflected and/or diffracted by the structure.

According to an aspect of the invention, there is provided a metrology method for measuring a parameter of a microscopic structure formed on a substrate, the method comprising: illuminating the structure with radiation from a supercontinuum light source and detecting radiation returned from the structure using a sensor.

According to an aspect of the invention, there is provided a lithographic apparatus arranged to transfer a pattern onto a substrate and comprising a metrology device for measuring a parameter of a microscopic structure on the substrate, the apparatus comprising a supercontinuum light source arranged to generate a measurement beam, an optical system arranged to direct the measurement beam onto the substrate and a sensor for detecting radiation reflected and/or diffracted by the structure.

According to an aspect of the invention, there is provided a process apparatus arranged to effect a process on a substrate and comprising a metrology device for measuring a parameter of a microscopic structure on the substrate, the apparatus comprising a supercontinuum light source arranged to generate a measurement beam, an optical system arranged to direct the measurement beam onto the substrate and a sensor for detecting radiation reflected and/or diffracted by the structure.

According to an aspect of the invention, there is provided a device manufacturing method comprising: measuring a parameter of a microscopic structure formed on a first substrate, by illuminating the structure with radiation from a supercontinuum light source and detecting radiation returned from the structure using a sensor; and transferring a pattern onto a second substrate using a lithographic process, a parameter of the lithographic process being determined on the basis of the measured parameter of the structure.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
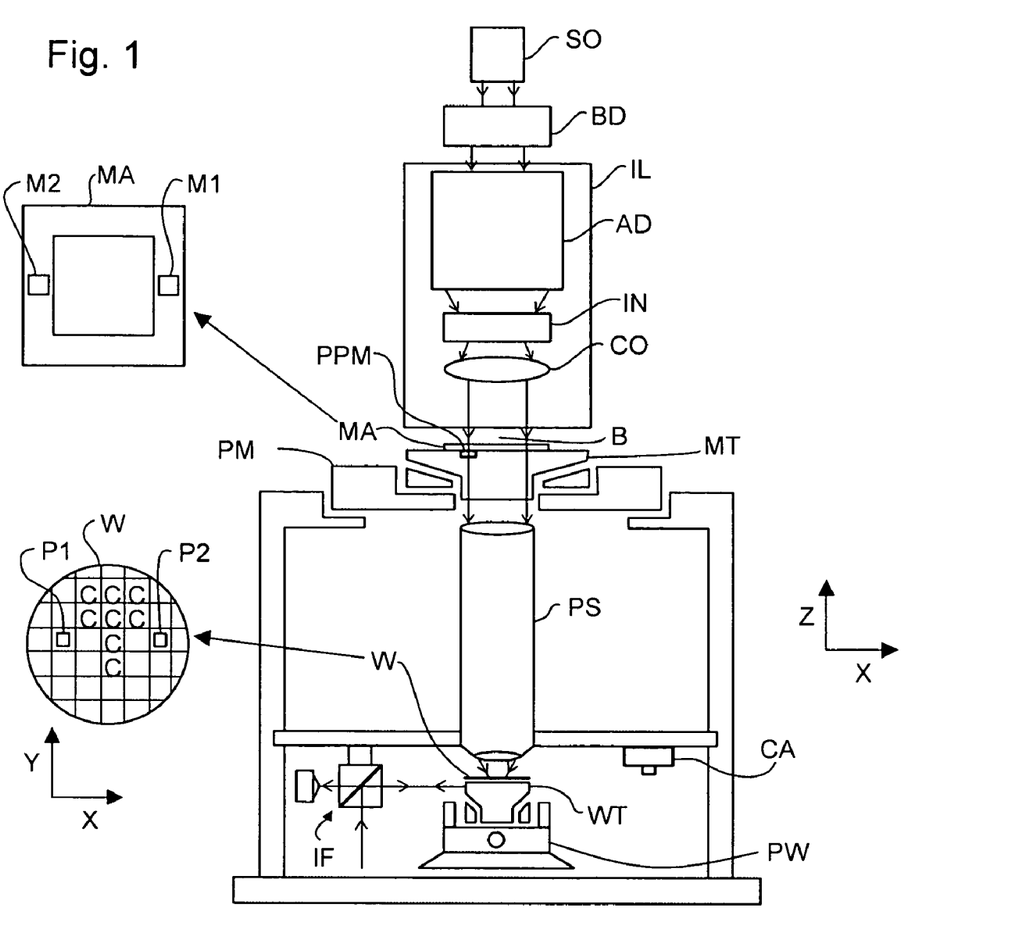
FIG. 1 depicts a lithographic apparatus according to an embodiment of the invention.

FIG. 1 schematically depicts a lithographic apparatus used in one embodiment of the invention. The apparatus comprises:

an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as $\sigma$-outer and $\sigma$-inner, respectively) of the intensity distribution in a pupil plane of the illuminator can be adjusted. In addition, the illuminator IL may comprise various other components, such as an integrator IN and a condenser CO. The illuminator may be used to condition the radiation bean, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
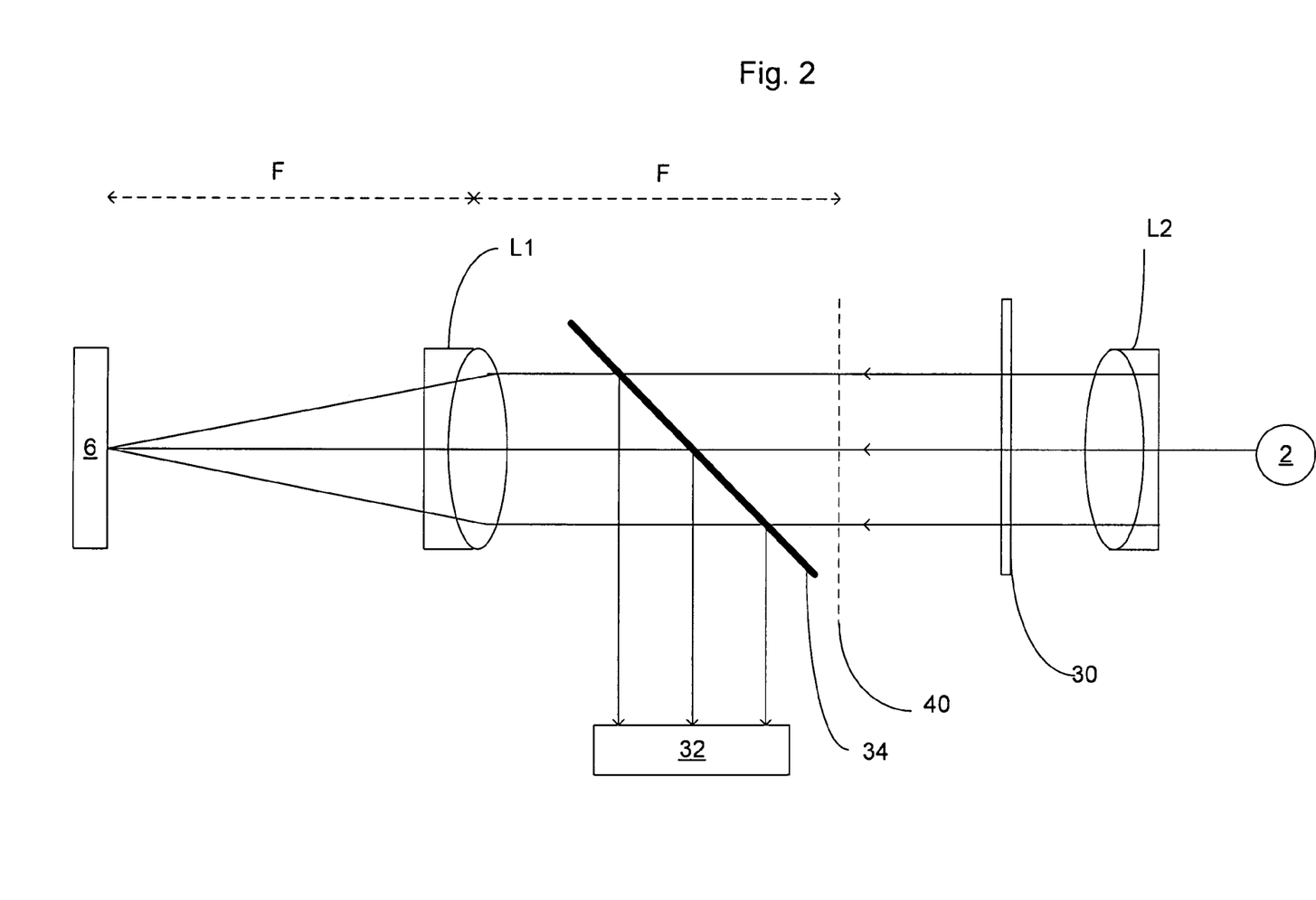
FIG. 2 depicts a scatterometer according to an embodiment of the invention.

A scatterometer arranged in accordance with an embodiment of the present invention is shown in FIG. 2. Save for the light source, which is described further below, the scatterometer is the same as that described in U.S. patent application Ser. No. 10/918,742, filed Aug. 16, 2004, which document is hereby incorporated by reference in its entirety. The light source 2 is focused using lens system L2 through interference filter 30 and is focused onto substrate 6 via a microscope objective lens L1. The radiation is then reflected via partially reflective surface 34 into a CCD detector 32 in the back projected pupil plane 40 in order to have the scatter spectrum detected. The pupil plane 40 is at the focal length of the lens system L1. A detector and high aperture lens are placed in the pupil plane. The pupil plane may be re-imaged with auxiliary optics since the pupil plane of a high-NA lens is usually located inside the lens.

The pupil plane of the reflector light is imaged on the CCD detector 32 with an integration time of, for example, 40 milliseconds per frame. In this way, a two-dimensional angular scatter spectrum of the substrate targets is imaged on the detector. The detector may be, for example, an array of CCD detectors or CMOS detectors. The processing of the spectrum gives a symmetrical detection configuration and so sensors can be made rotationally symmetrical. This allows the use of compact substrate tables because a target on the substrate can be measured at any rotational orientation relative to the sensor. All the targets on the substrate can be measured by a combination of a translation and a rotation of the substrate.

A set of interference filters 30 is available to select a wavelength of interest in the range of, say, 405-790 nm or even lower, such as 200-300 nm. Much longer wavelengths, e.g. about 1.5 µm could also be used. The interference filter may be tunable rather than comprising a set of different filters. A grating could be used instead of interference filters.

The substrate 6 may have on it a grating. The grating may be printed such that after development, the bars are formed of solid resist lines. The bars may alternatively be etched into the substrate. This pattern is sensitive to comatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process from knowledge of the printing step and/or other scatterometry processes.

Figure 3:
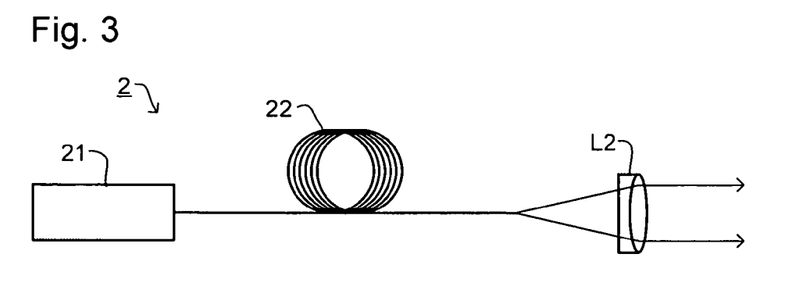
FIG. 3 depicts a light source useable in a scatterometer according to an embodiment of the invention.

In an embodiment of the invention, the light source 2 comprises a so-called "super-continuum" light source, an example of which is shown in FIG. 3. As shown in that figure, the light source 2 comprises a source laser 21 whose output is fed into a non-linear fiber 22 which mixes the light output by the source laser 21 in a non-linear manner so as to convert the relatively narrow input bandwidth into a much broader output bandwidth. The exact width of the broadband output from the non-linear fiber can be selected by selection of the type of source laser input, variation of the properties of the non-linear fiber and the length of fiber used. An output bandwidth of at least about 20 nm, or at least about 200 nm, with a lowest wavelength of less than about 400 nm is suitable for use in the present invention.

The non-linear fiber 22 may be a tapered fiber or a photonic bandgap fiber several centimeters to several kilometers in length. It can conveniently used to couple the measurement beam to the desired location and can be arranged to emit in a nearly pure $TEM_{00}$ mode enabling the beam to be focused on a very small spot on the substrate. Multimode fibers may also be used. Silicon waveguides and bulk materials may also be used in place of the non-linear fiber.

Suitable source lasers include both continuous beam lasers and pulsed beam lasers, with pulse lengths from greater than 1 ns to less than 15 fs and repetition rates from less than 10 Hz to greater than 1 kHz. Examples of suitable lasers are: erbium-doped fiber lasers, Q-switched lasers (e.g. Nd-Yag lasers), mode-locked lasers and Raman fiber lasers. The increased intensity of the illumination beam obtained using a supercontinuum source increases signal-to-noise ratios and allows a substantial increase in measurement speed and/or measurement accuracy. It also makes practicable measurements on latent marks in undeveloped resist. This facilitates in-line metrology, i.e. integration of the metrology sensor into the lithographic apparatus, potentially allowing reworking prior to development and/or corrections within a single batch. In other words, the metrology results can be used to adjust a parameter of a subsequent exposure on the same substrate (with or without reworking) or on a different substrate.

Figure 4:
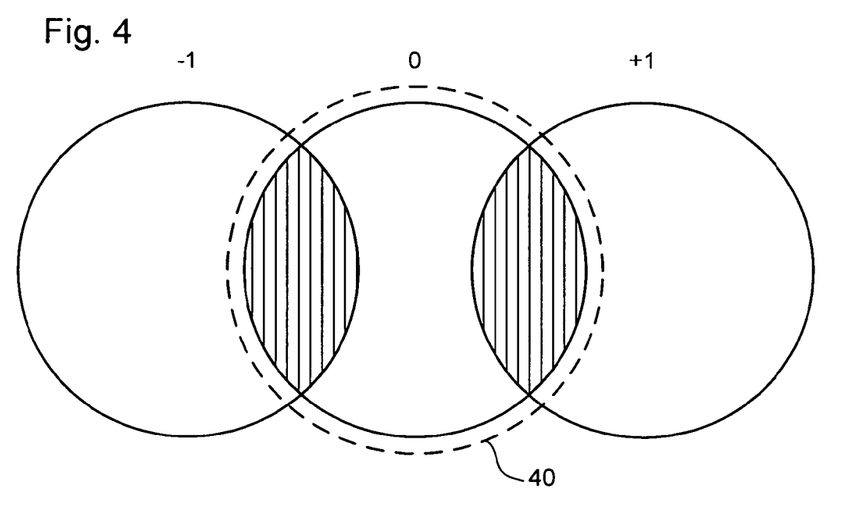
FIG. 4 depicts interference regions in a pupil plane of a scatterometer according to an embodiment of the invention.

In a particular embodiment of the invention, the spatial coherence of the beam generated by the supercontinuum light source is used to generate interference fringes that can significantly increase sensitivity. This is shown in FIG. 4. The objective lens L1 is set at a small defocus and arranged so that the zeroth and at least one of the first (in the illustrated arrangement both) diffraction orders produced by the test structure partially overlap in the pupil plane 40. In the overlapping region, indicated by hatching, interference fringes are formed. The occurrence of fringes in this arrangement is described further in *Principles of Optical Disc Systems* by G. Bouwhuis et al, Adam Hilger 1985 (ISBN 0-85274-785-3). For detection purposes the interference pattern has several advantages.

Firstly, in the small signal limit, i.e. when the phase depth of the test structure is small and the first order beam is of low intensity, the contrast of the fringe pattern depends linearly on the phase depth and is therefore higher than other detectors which have a quadratic dependence on phase depth.

Secondly, the position of the fringes is dependent on the lateral offset of the test structure so that a scanning stage can be used to enable detection of the position of the mark and two marks in different layers can then be used to detect overlay.

Thirdly, the fringe frequency depends on the defocus of the sensor with respect to the object lane of the test structure. The device can therefore be used to obtain depth information.

Fourthly, by using a compound overlay mark (two gratings positioned above or near each other in two different layers) asymmetry between the two overlap areas in the pupil plane 40 can be used for overlay detection.

The metrology device of embodiments of the invention can be incorporated into a lithographic apparatus, e.g. at the measurement station of a dual-stage apparatus, or a process device such as a PVD apparatus.

Figure 5:
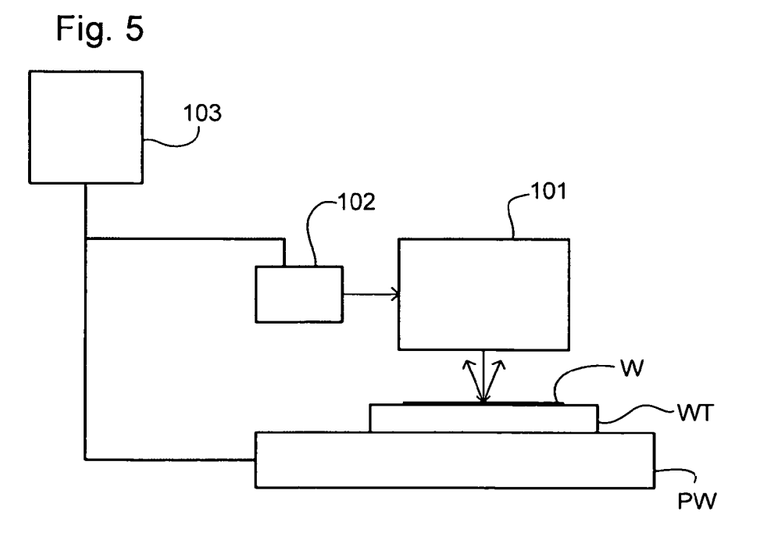
FIG. 5 depicts a scatterometer according to another embodiment of the invention.

In another particular embodiment of the invention, shown in FIG. 5, the speed of measurement of the scatterometer can be substantially increased by synchronizing the output pulses of the supercontinuum light source to movement of a stage carrying the substrate.

The scatterometer 101 is supplied with a pulsed measurement beam by supercontinuum light source 102 and makes measurements of markers on a substrate W which is held on a table WT. The table WT is scanned underneath the scatterometer 101 by positioning device PW which is connected to a controller 103. Controller 103 may either control the positioner PW to position the substrate table or may receive position information from a position measurement system (not shown) whilst the positioner is under the control of a separate controller. Either way, the controller is also connected to source 102 and controls source 102 to emit a pulse when the substrate W is in a position such that a marker is under the scatterometer. In this way "on-the-fly" measurements can be taken much more quickly that prior art arrangements which required markers to be positioned under the scatterometer and the substrate held still for long enough for a measurement to be taken.

Figure 6:
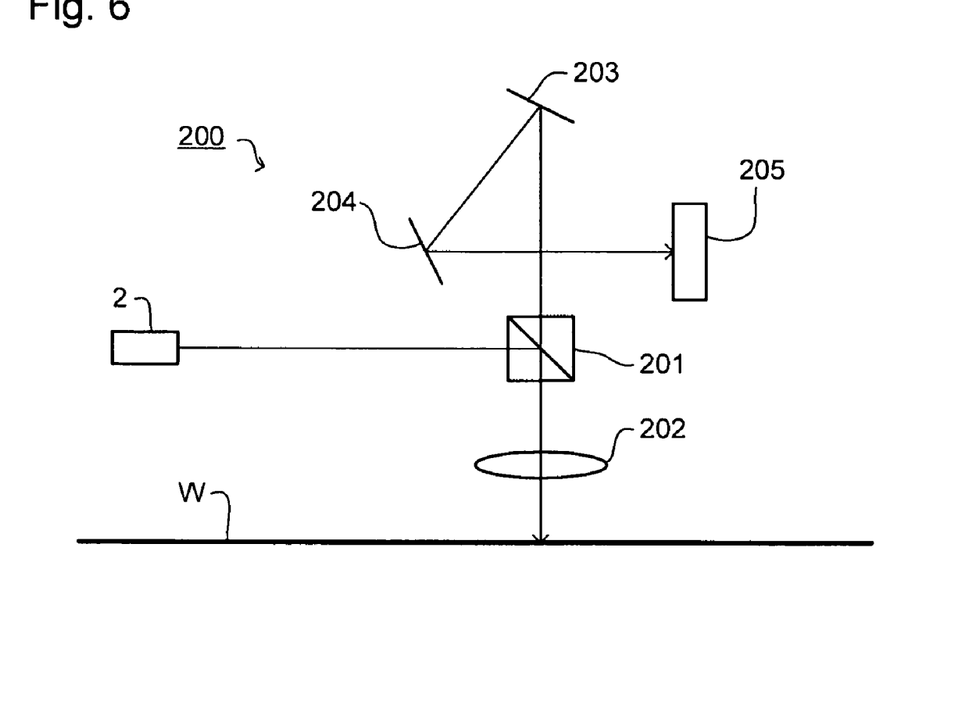
FIG. 6 depicts a scatterometer according to yet another embodiment of the invention.

Yet another particular embodiment of the invention comprises a scatterometer 200 of the spectroscopic reflectometer type, as shown in FIG. 6. In this device, the supercontinuum light source 2 supplies a high-power, broadband, well-collimated beam which is directed to a beam splitter 201, which reflects the beam towards the substrate W to be measured. A microscope objective 202 focuses the beam onto the substrate and collects the reflected light, directing it through beamsplitter 201 to a mirror 203, which reflects it to a grating 204. The grating 204 disperses the light onto a detector 205, e.g. a cooled CCD array. The output of the CCD array is an spectrum of the reflected light, i.e. a measurement of intensity as a function of wavelength, which can be used to deduce parameters of a structure on the substrate W, e.g. the linewidth of a grating, in a known manner, for example by comparison with a library of measurements form test structures or spectra calculated by simulation.

Scatterometer 200 is similar to known scatterometers except for the use of a supercontinuum light source; known scatterometers of this type have used Halogen or deuterium lamps, or both. Use of the supercontinuum light source increases the intensity of the incident beam, and hence the reflected light, allowing measurements to be taken more quickly. Scatterometer 200 may also be used in the system of FIG. 5.

Figure 7:
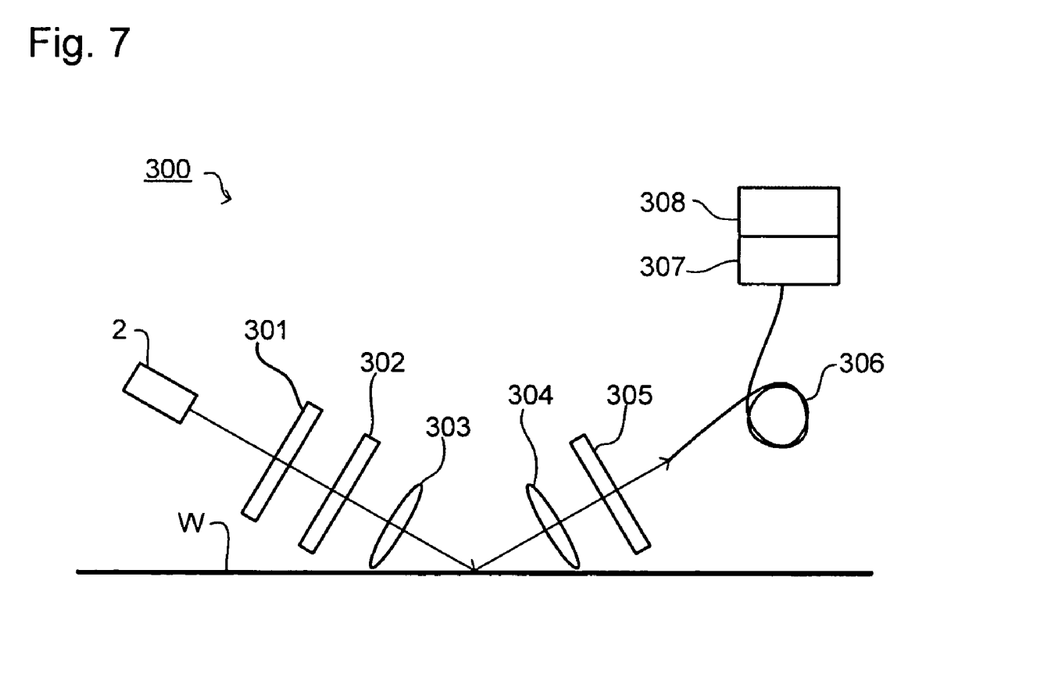
FIG. 7 depicts a scatterometer according to still another embodiment of the invention.

Still a further particular embodiment of the invention is scatterometer 300, shown in FIG. 7, which is of the spectroscopic ellipsometer type. In this device, the output of supercontinuum light source 2 is passed though a polarizer 301 so as to linearly polarize the beam, or clean up its polarization if already partially polarized. If the output of the supercontinuum light source 2 is already sufficiently polarized, polarizer 301 may be omitted. The polarized beam is then passed through a rotating compensator 302, to enable adjustment of the polarization direction, and is focused onto the substrate W to be inspected by lens 303. A collecting lens 304 collects the reflected light and directs it to a polarizing analyzer 305, after which an optical fiber 306 couples the light to a spectroscope 307 and detector array 308, e.g. a cooled CCD array.

The properties of the substrate W and the films or structures thereon, affect the intensity and polarization state—linearly polarized light becomes elliptically polarized—of the reflected light differently at different wavelengths. By rotating the analyzer, the scatterometer can provide measurements of intensity and ellipticity as functions of wavelength, providing information to enable reconstruction of structures on the substrate or deduction of parameters thereof, by known techniques.

Again, scatterometer 300 is similar to known scatterometer except for the use of a supercontinuum light source; known scatterometers of this type have used Xe arc or deuterium lamps, or both. Use of the supercontinuum light source increases the intensity of the incident beam, and hence the reflected light, allowing measurements to be taken more quickly. Scatterometer 300 may also be used in the system of FIG. 5.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A metrology apparatus for measuring a parameter of a microscopic structure on a substrate, comprising:
    a supercontinuum light source arranged to generate a measurement beam;
    an optical system arranged to direct the measurement beam onto the substrate; and
    a sensor for detecting radiation reflected and/or diffracted by the structure, wherein the sensor is arranged to detect interference fringes generated by overlapping of the zeroth diffraction order beam and at least one first diffraction order beam.

2. The metrology apparatus according to claim 1, wherein the supercontinuum light source comprises:
    a source laser arranged to generate a first beam; and
    a non-linear medium arranged to receive the first beam and generate a second beam, the second beam having a greater band width than the first beam.

3. The metrology apparatus according to claim 2, wherein the source laser comprises a continuous beam laser.

4. The metrology apparatus according to claim 2, wherein the source laser comprises a pulsed laser.

5. The metrology apparatus according to claim 4, further comprising:
    a positioner arranged to move the substrate relative to the sensor; and
    a controller arranged to synchronize the source to emit pulses when the substrate is in a desired position.

6. The metrology apparatus according to claim 2, wherein the non-linear medium comprises at least one optical element selected from the group consisting of doped-fibers, tapered fibers, photonic band-gap fibers and silicon-based waveguides.

7. The metrology apparatus according to claim 1, wherein the optical system comprises an objective lens, and the sensor comprises a a detector arranged to detect the spatial variation in intensity of radiation returned from the structure in a pupil plane of the objective lens.

8. The metrology apparatus according to claim 7, further comprising a second optical system arranged to re-image the pupil plane of the objective lens onto the detector.

9. The metrology apparatus according to claim 7, wherein the objective lens is arranged so that the image of the structure is out of focus on the detector.

10. The metrology apparatus according to claim 9, wherein the objective lens is arranged so that the zeroth and at least one first order of diffracted radiation returned from the test structure overlap in the pupil plane.

11. The metrology apparatus according to claim 9, wherein a frequency of the interference fringes depends on a defocus of the image of the microscopic structure.

12. The metrology apparatus according to claim 9, wherein a defocus of the image of the microscopic structure is used to obtain depth information.

13. The metrology apparatus according to claim 1, wherein the microscopic structure comprises at least two distinct gratings positioned above or near each other in at least two different layers.

14. The metrology apparatus according to claim 13, wherein an asymmetry between the interference fringes originating from two distinct gratings is used for overlay detection.

15. The metrology apparatus according to claim 1, wherein a contrast of the interference fringes depends linearly on a phase depth.

16. The metrology apparatus according to claim 1, wherein a position of the interference fringes depends on a lateral offset of the microscopic structure.

17. The metrology apparatus according to claim 1, wherein a lateral offset of the microscopic structure is used to detect overlay of measuring structures located on different layers.

18. The metrology apparatus according to claim 1, further comprising:
    a collecting optical system arranged to collect the radiation reflected and/or diffracted by the structure; and
    a wavelength dispersing device arranged to disperse the radiation collected by the collecting optical system according to wavelength, wherein the sensor is arranged to sense the intensity of the dispersed radiation as a function of wavelength.

19. The metrology apparatus according to claim 18, wherein the supercontinuum light source is arranged to generate a polarized measurement beam, and wherein the apparatus further comprises:
    a rotatable compensator arranged to rotate the direction of polarization of the measurement beam; and
    an analyzer arranged to analyze the polarization state of the radiation reflected and/or diffracted by the structure.

20. A metrology method for measuring a parameter of a microscopic structure formed on a substrate, the method comprising:
    illuminating the structure with radiation from a supercontinuum light source; and
    detecting radiation returned from the structure using a sensor, wherein the sensor is arranged to detect interference fringes generated by overlapping of the zeroth diffraction order beam and at least one first diffraction order beam.

21. A method according to claim 20, wherein said sensor is an angle-resolved scatterometer.

22. A method according to claim 21, wherein said scatterometer comprises an objective lens having a pupil plane, the objective lens being set at a defocus position such that the zeroth and at least one first diffraction order at least partially overlap in the pupil plane.

23. A method according to claim 20, wherein the structure is a structure formed on a substrate using a lithographic process.

24. A method according to claim 23, wherein the structure is selected from the group consisting of: alignment markers, CD-uniformity targets, overlay targets, diffraction gratings and device structures.

25. A method according to claim 23, wherein said structure is a latent image in a resist layer.

26. A method according to claim 20, wherein the parameter comprises a position of the structure on the substrate in at least one dimension.

27. A method according to claim 20, wherein the parameter comprises overlay.

28. A lithographic apparatus arranged to transfer a pattern onto a substrate and comprising a metrology device for measuring a parameter of a microscopic structure on the substrate, the apparatus further comprising:
   a supercontinuum light source arranged to generate a measurement beam;
   an optical system arranged to direct the measurement beam onto the substrate; and
   a sensor for detecting radiation reflected and/or diffracted by the structure, wherein the sensor is arranged to detect interference fringes generated by overlapping of the zeroth diffraction order beam and at least one first diffraction order beam.

29. A process apparatus arranged to effect a process on a substrate and comprising a metrology device for measuring a parameter of a microscopic structure on the substrate, the apparatus further comprising:
   a supercontinuum light source arranged to generate a measurement beam;
   an optical system arranged to direct the measurement beam onto the substrate;
   and a sensor for detecting radiation reflected and/or diffracted by the structure,
   wherein the sensor is arranged to detect interference fringes generated by overlapping of the zeroth diffraction order beam and at least one first diffraction order beam.

30. A device manufacturing method, comprising: measuring a parameter of a microscopic structure formed on a first substrate, by:
   illuminating the structure with radiation from a supercontinuum light source; and
   detecting radiation returned from the structure using a sensor, wherein the sensor is arranged to detect interference fringes generated by overlapping of the zeroth diffraction order beam and at least one of first diffraction order beams; and
   transferring a pattern onto a second substrate using a lithographic process, a parameter of the lithographic process being determined on the basis of the measured parameter of the structure.

31. A method according to claim 30, wherein the first substrate is the second substrate.

32. A method according to claim 30, wherein the first substrate is not the second substrate.

* * * * *

UNITED STATES PATENT AND TRADEMARK OFFICE
CERTIFICATE OF CORRECTION

PATENT NO. : 7,403,293 B2
APPLICATION NO. : 11/478300
DATED : July 22, 2008
INVENTOR(S) : Pellemans et al.

It is certified that error appears in the above-identified patent and that said Letters Patent is hereby corrected as shown below:

Column 10
Line 8, "comprises a a detector" replace with --comprises a detector--.

Signed and Sealed this

Twenty-third Day of December, 2008

JON W. DUDAS
*Director of the United States Patent and Trademark Office*